United States Patent [19]

Tansey

[11] Patent Number: 4,681,590
[45] Date of Patent: Jul. 21, 1987

[54] FEMORAL STEM PROSTHESIS

[76] Inventor: John Tansey, 6019 Foxhall Farm Rd., Baltimore, Md. 21228

[21] Appl. No.: 875,628

[22] Filed: Jun. 18, 1986

[51] Int. Cl.⁴ .............................................. A61F 2/32
[52] U.S. Cl. ................................... 623/23; 128/92 YY
[58] Field of Search ................................... 623/16-23; 128/92; 433/172-176

[56] References Cited

U.S. PATENT DOCUMENTS

| | | | |
|---|---|---|---|
| 2,685,877 | 8/1954 | Dobelle | 623/23 |
| 3,024,785 | 3/1962 | Dobelle | 623/23 |
| 3,846,846 | 11/1974 | Fischer | 623/23 |
| 4,054,955 | 10/1977 | Seppo | 623/22 |
| 4,101,985 | 7/1978 | Baumann et al. | 623/23 |
| 4,187,559 | 2/1980 | Grell et al. | 623/18 |
| 4,237,875 | 12/1980 | Termanint | 128/92 |
| 4,298,993 | 11/1981 | Kovaleva et al. | 623/23 |
| 4,314,381 | 2/1982 | Koeneman | 623/18 |
| 4,404,692 | 9/1983 | Eftekhar | 623/18 |
| 4,520,511 | 6/1985 | Gianezio et al. | 623/22 |

FOREIGN PATENT DOCUMENTS

| | | | |
|---|---|---|---|
| 0728855 | 5/1980 | U.S.S.R. | 433/173 |
| 1041102 | 9/1983 | U.S.S.R. | 128/92 |

Primary Examiner—Richard J. Apley
Assistant Examiner—David J. Isabella
Attorney, Agent, or Firm—Nixon & Vanderhye

[57] ABSTRACT

A femoral stem prosthesis designed for secure fixation to the walls of the intramedullary canal of the femur. The prosthesis has an elongated stem portion, with a ball-shaped head, which carries one or more elongated resilient spring strips which are acted upon by an adjustable screw actuator to cause the spring strips to bow outwardly into engagement with the canal walls.

14 Claims, 5 Drawing Figures

FIG. 4
FIG. 5
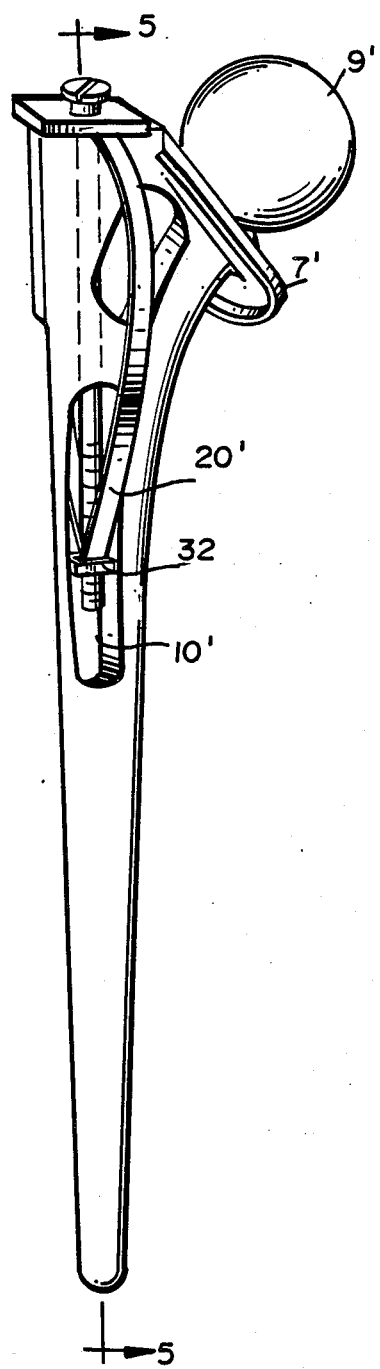
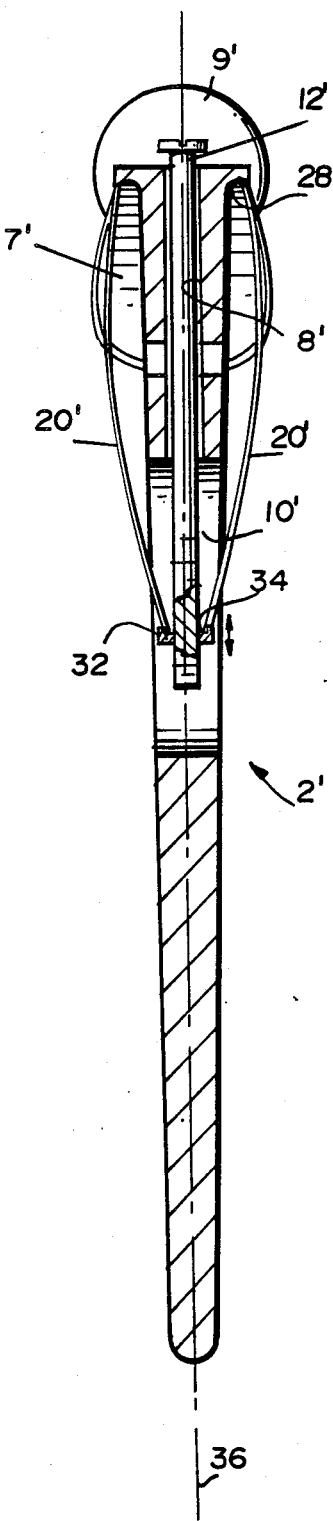

FEMORAL STEM PROSTHESIS

BACKGROUND OF THE INVENTION

This invention relates to a hip prosthesis to be fixed to the femoral joint, and more particularly, to a femoral stem prosthesis for insertion into the intramedullary canal of the femur.

The use of hip joint prosthesis having ball-shaped head portions and stems which are fixed within the intramedullary canal is well-known. Typically, the prosthesis is secured within the canal with the aid of special cement. See, for example, U.S. Pat. No. 4,404,692. It is also known to secure hip joint prosthesis by various mechanical means including screws (U.S. Pat. No. 4,101,985), expandable stems (U.S. Pat. No. 4,520,511), expandable stem segments (U.S. Pat. No. 3,846,846) and extendable leg anchors (U.S. Pat. No. 3,024,785); see also U.S. Pat. No. 2,685,877. Nevertheless, loosening of the femoral component of the total hip replacement, caused by rotary or torsion forces about the upper end of the femoral shaft, continues to be a problem. Once the prosthesis has been loosened, it must be surgically reset.

According to the present invention, a femoral stem prosthesis is provided having an elongated stem portion for insertion into the intramedullary canal of the femur. The elongated stem portion has upper and lower ends, a longitudinal axis, and a threaded bore extending generally along the longitudinal axis from the upper end of the stem portion to a point within an elongated aperture located generally in the upper half of the stem portion. The stem is also provided with a plurality of retaining notches formed in laterally aligned pairs along opposite sides of the stem below the elongated aperture. Anchoring means are provided for firmly attaching the prosthesis to the surrounding walls of the intramedullary canal in the form of one or more elongated resilient spring steel strips carried by the stem portion. The stem portion also carries an adjustable actuator screw in the threaded bore. The adjustable actuator screw at its lower end engages a plunger slidably received in the bore. The plunger is formed with an enlarged retaining collar at an end remote from the screw engagement, the collar being free to move axially within the elongated aperture formed beneath the threaded bore. Each of the elongated resilient spring steel strips have a first end received in the retaining collar and a second end received in one of the retaining notches formed in the stem portion. The construction is such that upon rotation of the adjustable actuator screw to effect downward movement of the plunger, pressure is applied through the retaining collar on the elongated resilient spring strips to cause the strips to bow outwardly in a direction perpendicular to the longitudinal axis of the stem. As the adjustable actuator screw is rotated further, the spring steel strips continue to expand outwardly until they firmly engage the walls of the intramedullary canal. Additional apertures may be formed in the stem portion to provide ample room for ingrowth of bone tissue in and around the spring steel strips and the prosthesis itself to thereby permit the formation of a large, strong, bony resistant mass to further counteract the torsion forces which would otherwise tend to loosen the prosthesis.

According to the present invention, at least two and as many as three laterally aligned pairs of retaining notches are formed along the length of the stem portion to accommodate spring strips of different lengths. In this way, the length and location of the spring strips, and therefore the expansion capability of the device, may be selected as required. In addition, the number of spring strips may be varied. In a preferred embodiment, at least one pair of spring strips of equal length are utilized. In their expanded state, the spring strips form a generally elliptical shape which provides a particularly strong anchoring configuration. it is to be understood that as many as three pair of spring strips may be used concurrently.

The upper end of the stem portion has a ball-shaped head of a conventional type.

In an alternative embodiment of the invention, a modified actuator screw is used which eliminates the need for the spring retaining notches formed in the stem. The screw is rotatably received within a smooth bore formed in the stem. The lower portion of the screw extends into a slot formed in the stem and is threaded in order to receive a modified nut which is held against rotation in the slot but is free to move axially therein. In this embodiment, the spring strips are held between a flange formed at the upper end of the stem and an upwardly facing recess formed in the axially moveable nut. Rotation of the actuator screw moves the nut upwardly causing the spring strips to bow outwardly in a manner similar to that described above.

BRIEF DESCRIPTION OF THE DRAWINGS

FIG. 4 is a persective view of an alternative exemplary embodiment of the invention; and FIG. 5 is a sectional view of the stem portion taken along the line 5—5 thereof of the FIG. 4 embodiment.

DETAILED DESCRIPTION OF THE DRAWINGS

Figure 3:
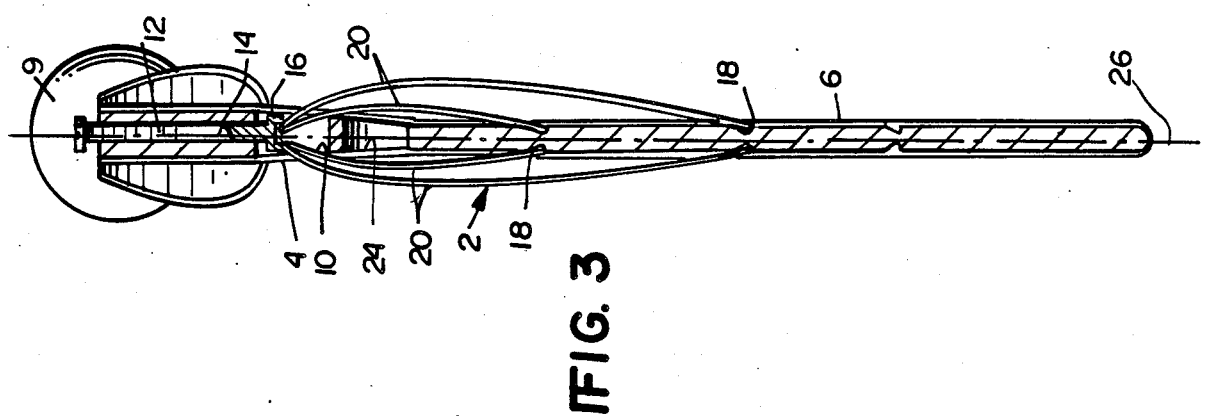
FIG. 3 is a sectional view taken along the line 3—3 of FIG. 2 but with two pair of spring steel strips attached and in the expanded position.
Figure 2:
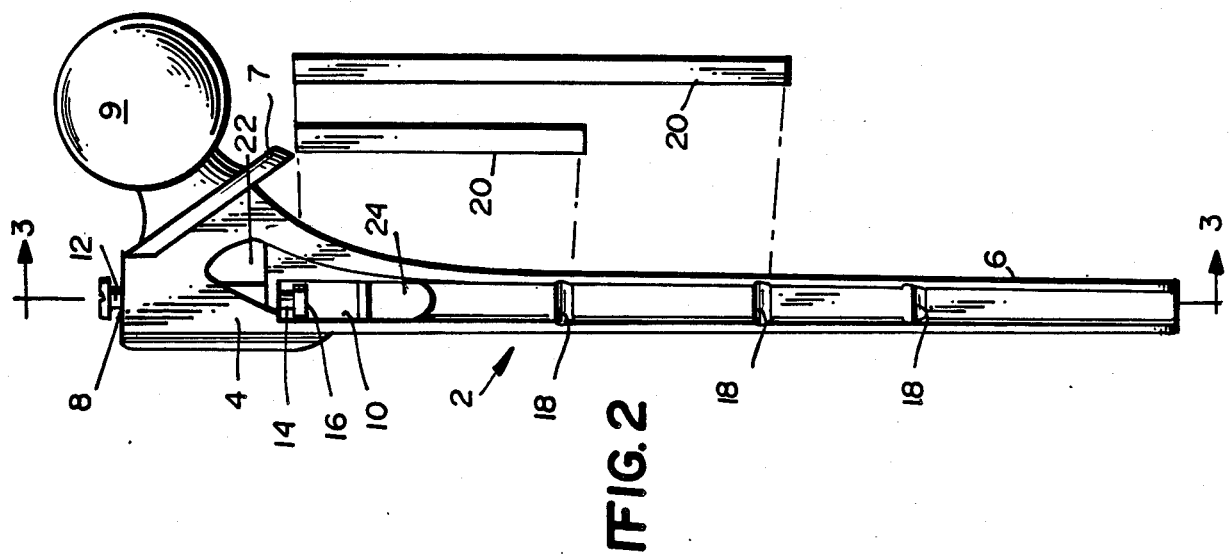
FIG. 2 is a side view of the prosthesis of FIG. 1 with the spring steel strips detached from the stem portion, and with the femoral head being shown.
Figure 1:
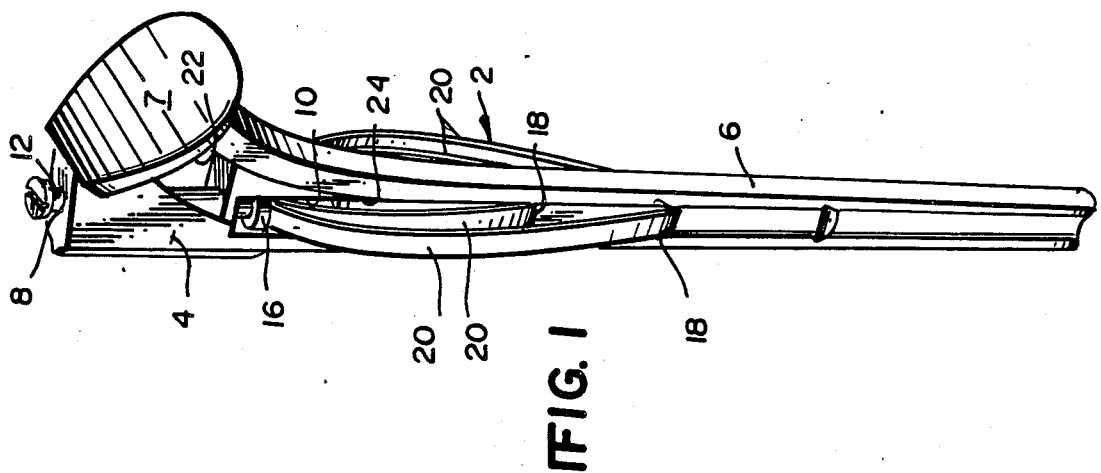
FIG. 1 is a perspective view of an exemplary prosthesis according to the invention.

Referring now to the exemplary embodiment illustrated in FIGS. 1 through 3 of the drawings, the prosthesis includes an elongated stem portion 2 having an enlarged upper end 4 and a narrower lower end 6. The upper enlarged end of the stem portion is formed with a conventional ball-shaped (femoral) head 9 extending from ridge 7. (Head 9 is not shown in FIG. 1). The elements 2, 4, 6, 7, and 9 are preferably of biocompatible metal. The stem is provided with a threaded bore 8 extending from the upper end of the stem portion and terminating in an elongated slot 10 formed in the upper half of the stem portion. Threadably received within an upper portion of the bore 8, is an adjustable actuator screw 12 provided at one end with a conventional screw driving head. Slidably received within a lower portion of the bore 8 for engagement with the other end of the screw is a plunger 14. The lower end of the plunger is provided with a recessed, spring strip retaining collar 16 which moves axially within the slot 10. The stem portion 2 is also provided with a plurality of retaining notches 18 which are arranged in laterally aligned pairs on opposite sides of the stem portion 2. While three pairs of laterally aligned notches are shown in the drawings, it is understood that the number of notches may be varied as needed.

Anchoring means for firmly fixing the prosthesis against the walls of the intramedullary canal are provided in the form of elongated resilient spring strips 20. These strips, which may be constructed of spring steel, are held in place by engaging one end thereof in one of the spring retaining notches formed on the stem portion and engaging the other end thereof in the spring retaining collar 16 provided at the lower end of the plunger 14.

It is to be understood that the number and length of spring steel strips used to anchor the prosthesis to the walls of the intramedullary canal may also be varied as needed.

In operation, it may be seen that when the adjustable screw actuator 12 is rotated to effect downward movement thereof, plunger 14 and spring retaining collar 16 move downwardly to exert pressure against the elongated resilient spring strips causing them to bow outwardly in a direction perpendicular to the longitudinal axis 26 of the stem portion. Note that by changing the length of the strips, the expansion capability of the debive is changed as well. In addition, the length of the strips can be correlated to the amount of outward bowing which will be obtained. For example, with a 10 cm. long spring strip, a maximum outward expansion of 2.5 cm. will obtain when the effective length of the strip is shortened to 5 cm. by the actuator screw 12.

In a preferred embodiment, a matched pair of spring strips 20 of equal length are used in association with a laterally aligned pair of spring retaining notches formed in the stem portion. In the expanded state, a generally elliptical shape is formed by the pair of spring strips. This configuration provides a particularly strong anchoring configuration which is effective in resisting the rotational and torsional forces encountered by the femoral insert.

Additional apertures 22, 24 may be provided in the elongated stem portion of the prosthesis which, along with the bowed configuration of the anchoring strips, provides ample room for ingrowth of living bony tissue in and around the prosthesis to form a large strong bony resistant mass which serve to further counteract torsional as well as compressive forces encountered by the prosthesis.

In the alternative embodiment illustrated in FIGS. 4 and 5, there is shown a modified actuating means for expanding a pair of spring strips. A smooth bore 8' is provided in the elongated stem portion 2', the smooth bore terminating in an elongated slot 10'. The stem portion 2' is further provided at its upper end with a flange defining an annular, downwardly opening recess 28. An adjustable screw actuator 12' is slideably received within the bore 8', the screw being provided at its upper end with a conventional screw driving head. Threadably mounted on the actuator screw is a modified nut 32 provided with an annular recess 34 facing upwardly in opposing relationship to the downwardly opening recess 28 formed on the elongated stem portion 2'. The nut 32 has a peripheral size and shape such that it is held against rotation in the slot 10'. In this embodiment, the spring steel strips are mounted with their first ends received within the recess 28, and their second ends received within the recess 34 provided in the nut 32. As the screw actuator 12' is rotated, nut 32 is free to move up or down, depending on the direction of rotation of the screw, within the elongated slot 10'. As the nut 32 moves in an upward direction, the pair of spring steel strips will bow outwardly at a point intermediate their ends in a direction perpendicular to the longitudinal axis 36 of the stem in the same manner as in the embodiment illustrated in FIGS. 1 through 3.

While the invention has been herein shown and described in what is presently conceived to be the most practical and preferred embodiment thereof, many modifications may be made thereof within the scope of the invention, which scope is to be accorded the broadest interpretation of the appended claims so as to encompass all equivalent structures and devices.

What is claimed is:

1. A femoral stem prosthesis comprising:
   (a) an elongated stem portion adapted to be inserted into the intramedullary canal of the femur and firmly attached to surrounding walls thereof;
   (b) anchoring means associated with the stem, said anchoring means comprising at least one elongated resilient member which has a first end in operative engagement with the actuating means, and a second end attached to the stem;
   (c) actuating means for causing outward bowing of the anchoring means into firm engagement with the surrounding walls of the canal, said actuating means comprising an actuator screw threadably mounted within a bore formed in the stem, a plunger slidably received within the bore with one end of the plunger in axial engagement with the actuator screw, and the other end of the plunger provided with a retaining collar adapted to receive the said first end of said at least one elongated resilient member.

2. A femoral stem prosthesis according to claim 1 wherein the at least one elongated resilient member comprises a spring steel strip. of the plunger in engagement with the actuator screw, and the other end of the plunger provided with a retaining collar adapted to receive the said first end of the one or more elongated resilient members.

3. A femoral stem prosthesis according to claim 1 wherein the stem portion has a longitudinal axis, the actuating screw mounted for movement along said axis so that rotation of the screw to effect downward movement of the plunger exerts pressure through said retaining collar on the said at least one elongated, resilient member to cause outward bowing intermediate the ends thereof in a direction perpendicular to the longitudinal axis of the stem portion.

4. A femoral stem prosthesis according to claim 1 wherein a plurality of retaining notches are formed in predetermined, laterally aligned locations along opposite sides of the stem portion.

5. A femoral stem prosthesis according to claim 4 wherein the anchoring means comprises a pair of elongated resilient members, the said second ends of said elongated resilient members received in a laterally aligned pair of retaining notches so that upon outward bowing of the elongated resilient members caused by said actuating means, a generally elliptical shape is formed by said pair of resilient members.

6. A femoral stem prosthesis according to claim 6 wherein at least two pair of laterally aligned retaining notches are formed along the stem for accommodating elongated resilient members of different lengths.

7. A femoral stem prosthesis according to claim 1 wherein said stem portion has a ball-shaped head portion.

8. A femoral stem prothesis according to claim 1 wherein the actuating means comprises an actuator screw rotatably received within a smooth bore formed in the stem, said actuator screw provided with a driving head at one end and a nut threadably mounted on the other end, said nut fixed against rotation with respect to the stem, and the said at least one elongated resilient member operatively connected between the nut and a flange formed on the stem.

9. A femoral stem prosthesis according to claim 8, wherein the said at least one elongated resilient member comprises a spring steel strip.

10. A femoral stem prosthesis according to claim 8, wherein the stem portion has a longitudinal axis, the nut mounted for movement along the axis upon rotation of the actuator screw to exert pressure on the one or more elongated resilient members to cause outward bowing intermediate the ends thereof in a direction perpendicular to the longitudinal axis of the stem portion.

11. A femoral stem prosthesis according to claim 8, wherein the anchoring means comprises a pair of elongated reslient members which combine to form a generally elliptical shape when in an outwardly bowed operative position.

12. A femoral stem prosthesis for insertion into the intramedullary canal of the femur, said prosthesis comprising:

(a) an elongates stem portion having a ball-shaped head and having a longitudinal axis, said stem portion having upper and lower ends; and threaded bore extending from the upper end of the stem portion to a point within an elongated aperture located in the upper half of the stem portion; and a plurality of retaining notches formed in laterally aligned pairs along opposite sides of the stem portion below the elongated aperture;

(b) anchoring means for firmly attaching the prosthesis to surrounding walls of the intramedullary canal, said anchoring means comprising at least·one elongated resilient member;

(c) actuating means for effecting movement of said anchoring means to an operative position, said actuating means comprising an actuator screw threadably received within said bore and a plunger slidably received within said bore, an upper end of the plunger in engagement with a lower end of said actuator screw, said plunger provided at a lower end with a retaining collar moveable axially within said elongated aperture; wherein said at least one elongated resilient member has a first end received within the retaining collar and a second end received in one of the retaining notches formed in the stem portion so that upon rotation of the screw to effect downward movement of the plunger, pressure is exerted through the retaining collar on the said at least one elongated resilient member to cause outward bowing thereof in a direction perpendicular to the longitudinal axis of the stem to an operative position wherein the prosthesis is secured to the surrounding walls of the canal.

13. A femoral prosthesis according to claim 12 wherein the anchoring means comprises at least a pair of elongated resilient members, the second ends of which are received in one of said laterally aligned pairs of retaining notches so that a generally elliptical shape is formed by said pair of members in said operative position.

14. A femoral prosthesis according to claim 13 wherein the anchoring means comprises at least three elongated resilient members, and wherein at least two pair of retaining notches are formed in the stem portion for accommodating elongated resilient members of different lengths.

* * * * *